United States Patent [19]

Wagner

[11] Patent Number: 5,597,554
[45] Date of Patent: Jan. 28, 1997

[54] ORAL HYGIENE SYSTEM

[75] Inventor: Eugene C. Wagner, Mount Kisco, N.Y.

[73] Assignee: Dental Concepts Inc., Elmsford, N.Y.

[21] Appl. No.: 225,735

[22] Filed: Apr. 11, 1994

Related U.S. Application Data

[63] Continuation-in-part of Ser. No. 50,565, Apr. 21, 1993, Pat. No. 5,302,374.

[51] Int. Cl.$^6$ .............................. A61K 9/16; A61K 9/18
[52] U.S. Cl. .............................. 424/53; 424/49; 424/52; 424/57
[58] Field of Search .............................. 424/49–58

[56] References Cited

U.S. PATENT DOCUMENTS

| | | | |
|---|---|---|---|
| 4,788,052 | 11/1988 | Ng et al. | 424/53 |
| 4,839,156 | 6/1989 | Ng et al. | 424/53 |
| 4,839,157 | 6/1989 | Ng et al. | 424/53 |
| 5,084,268 | 1/1992 | Thaler | 424/53 |
| 5,122,365 | 6/1992 | Murayama | 424/49 |
| 5,171,564 | 12/1992 | Nathou et al. | 424/53 |
| 5,208,010 | 5/1993 | Thaler | 424/53 |
| 5,240,415 | 8/1993 | Haynie | 433/216 |
| 5,256,402 | 10/1993 | Prencipe et al. | 424/53 |
| 5,264,205 | 11/1993 | Kelly | 424/53 |
| 5,279,816 | 1/1994 | Churat et al. | 424/53 |
| 5,302,374 | 4/1994 | Wagner | 424/52 |
| 5,302,375 | 4/1994 | Viscio | 424/53 |
| 5,401,495 | 3/1995 | Murayama | 424/49 |

FOREIGN PATENT DOCUMENTS

| | | |
|---|---|---|
| 202359 | 11/1986 | European Pat. Off. . |
| 520545 | 12/1992 | European Pat. Off. . |
| 1416782 | 12/1975 | United Kingdom . |

OTHER PUBLICATIONS

Printout Abstracts of FDC Reports Rose Sheet Oct. 28, 1991, Advertising Age Oct. 21, 1991 p. 3.
Adweek Natl Mktng Ed 27(16):8 Mar. 31, 1986; Adweek East. Ed. 27(3):40 Jan. 20, 1986.
Advertising Age 56(95):3,72 Dec. 9, 1985; Dagnoli Advertising Age Oct. 21, 1991 p. 3.
PR Newswire Oct. 19, 1992 p. 1; Product Alert Aug. 24, 1992; PR Newswire Mar. 21, 1993.
FDC Reports Rose Sheet May 4, 1992; Business Journal (Phoenix, AZ) p. 7 Sep. 7, 1992.
Business Journal (Phoenix, AZ) p. 2 May 1992, Food & Drug Packaging p. 2 Mar. 1992.
Lookout (Non–Foodsed.) p. 118NF–91 Jul. 23, 1991.
"Mentadent" Reg. TM. 1832568 Registered Apr. 26, 1994 first use in common Nov. 30, 1991.
"Mentadent" Reg. TM. 1827994 Registered Mar. 29, 1994 first use in common Nov. 30, 1991.
"Perigel" Reg. TM. 1724931 Registered Oct. 20, 1992 first use in common Jul. 1988.
"Gumbident" Reg. TM. 1552434 Registered Aug. 22, 1989 first use in common May 1, 1987.
"Periogene" Reg. TM. 1350230 Registered Jul. 23, 1985 first use in common Nov. 13, 1984.

*Primary Examiner*—Shep K. Rose
*Attorney, Agent, or Firm*—Natter & Natter

[57] ABSTRACT

A conventional toothpaste is dispensed on a toothbrush along with a quantity of an abrasive free dentifrice containing a peroxide compound as an active constituent. Abrasion constituents of the conventional toothpaste interact with the peroxide compound constituent of the dentifrice to accelerate the breakdown of the peroxide compound constituent and the release of active oxygen. The employment of an abrasive free base in the peroxide compound dentifrice also results in a significant reduction in dentin abrasion levels as compared with the conventional toothpaste alone.

16 Claims, No Drawings

ORAL HYGIENE SYSTEM

RELATED APPLICATION

This application is a continuation-in-part of application Ser. No. 08/050,565, filed Apr. 21, 1993, now U.S. Pat. No. 5,302,374 issued Apr. 12, 1994 and incorporated herein by reference.

BACKGROUND OF THE INVENTION

1. Field of the Invention

This invention relates generally to dentifrices and more particularly to a system employing a mixture of conventional toothpaste in combination with a dentifrice preparation having a peroxide compound as an active constituent.

2. Background History

The efficacy of peroxide compounds in oral hygiene has been long recognized. Such compounds have proven useful in the treatment of gingivitis, oral lesions, periodontitis, herpetic stomatitis, oral malodor and also in combatting plaque. Additionally, peroxide compounds have been utilized for oral cosmetic purposes such as tooth whitening. The release of active oxygen from a peroxide dentifrice in the oral cavity is believed to be primarily associated with the exposure of the peroxide to the enzyme catalase.

Problems encountered with respect to providing stable shelf life for such dentifrices were addressed in U.S. Pat. No. 5,804,268 issued Jan. 28, 1992 to the assignee of the instant application.

While the abrasive free peroxide based dentifrice formulations disclosed in such patent have proven efficacious for routine oral hygiene and cosmetic purposes, the Applicant has recognized the desirability of accelerating the breakdown of the peroxide compound constituent and the release of oxygen within the oral cavity. The Applicant has also recognized that in recent times, larger proportions of abrasives have been employed in conventional toothpastes. This has resulted in a concomitant increase in the potential for abrasion damage to tooth structure.

A need has been established for providing a system whereby efficacious cleansing of tooth surfaces can be achieved with reduced dentin abrasion levels.

SUMMARY OF THE INVENTION

In compendium, the invention comprises an oral hygiene system whereby a quantity of dentifrice comprising a peroxide compound as an active ingredient is placed upon the bristles of a toothbrush along with a quantity of conventional toothpaste having from approximately 20% to 50% abrasive constituent comprising a metal salt.

The abrasive constituents of the conventional toothpaste function to accelerate the decomposition of the peroxide compound constituent of the dentifrice while the peroxide dentifrice functions to reduce the dentin abrasion levels of the conventional toothpaste. The combined dentifrice and toothpaste synergistically function with enhanced deployment of active oxygen and with reduced dentin abrasion.

From the foregoing summary it will be appreciated that it is an aspect of the present invention to provide a system for oral hygiene which is not subject to the disadvantages of the background history aforementioned.

To provide a system for oral hygiene of the general character described which produces gentle cleansing of tooth surfaces is a consideration of the present invention.

A feature of the present invention is to provide a system for oral hygiene of the general character described which achieves efficacious results in the treatment and prevention of gum disease.

A consideration of the present invention is to provide a system for oral hygiene of the general character described which provides enhanced generation of oxygen from a peroxide dentifrice constituent within the oral cavity.

Another aspect of the present invention is to provide a system for oral hygiene of the general character described which is simple to practice.

To provide a system for oral hygiene of the general character described which enhances the flavor of a conventional toothpaste is another feature of the present invention.

Other aspects, features and considerations of the present invention in part will be obvious and in part will pointed our hereinafter.

With these ends in view, the invention finds embodiment in the various combinations of elements, arrangements of constituents and series of steps by which the aspects, features and considerations aforementioned and certain other aspects, features and considerations are attained, all with reference to the following description of the preferred embodiments and the scope of which will be more particularly pointed out and indicated in the appended claims.

DESCRIPTION OF THE PREFERRED EMBODIMENTS

The present invention provides a system for oral hygiene whereby a dentifrice which includes a peroxide compound as its active constituent is placed in contact with a conventional toothpaste having, as an abrasive agent, between approximately 20% to 50% of a metal salt. The mixing of the peroxide containing dentifrice with the conventional toothpaste within the oral cavity during tooth brushing causes accelerated release of oxygen by interacting with the peroxide constituent and/or by increasing the alkalinity level of the combined mixed formulation as compared with the pH level of the peroxide compound containing dentifrice alone.

The peroxide compound containing dentifrice may comprise a tooth whitening dentifrice as disclosed in U.S. Pat. No. 5,084,268, such as the commercially available hydrogen peroxide dentifrice sold under the registered trademark STAY WHITE®. STAY WHITE® dentifrice is a non-abrasive dentifrice comprising a blend of from about 2% to 35% corn starch, which functions as a jelling agent, a thickener, a filler and a binder, from 5% to 30% sorbitol which functions as a humectant and sweetening agent, from 0.2% to 10% hydrogen peroxide, from 0.2% to 4% Carbomer 940 which comprises a gum and jelling agent, 0.1% to 2% flavor, from 0.2% to 2% sodium laurel sulfate, which functions as a foaming and surfactant agent, from 0% to 0.25% potassium sorbate which functions as a preservative, 0.1% to 0.25% sodium benzoate which functions as a preservative and deionized water in a sufficient quantity. Additionally, a water softening chelating agent such as EDTA (approximately 0.1%) may be employed.

Many other peroxide compound containing dentifrices do not contain abrasive polishing agents since such materials activate the rapid decomposition of the peroxide compounds, resulting in premature release of oxygen. Illustrative of further non-abrasive dentifrices containing peroxide compounds are the dentifrices disclosed in U.S. Pat. Nos. 4,980,152; 4,839,156; 4,522,805 and 4,567,036 all of which are incorporated herein by reference.

U.S. Pat. No. 4,980,152 discloses a non-abrasive aqueous oral gel composition comprising from about 0.5 to about 10% by weight urea peroxide or hydrogen peroxide and from about 0.01 to 2% by weight of a fluoride providing compound. The composition further includes a thickening agent such as carboxy polymethylene, a non-ionic surfactant such as PLURONIC F127, alkali soluable cellulose ethers as viscosity increasing agents, potassium phosphate as a buffering agent and glycerine as a carrier and flavoring and sweetening agents.

U.S. Pat. No. 4,839,156 discloses an aqueous dental gel containing 18–25% by weight of a polyoxyethylene polypropylene block copolymer gelling agent, hydrogen peroxide, 15–40% by weight of a polyethylene glycol humectant, flavor, sweetening agent and a non-ionic surfactant as the essential ingredients.

U.S. Pat. Nos. 4,522,805 and 4,567,036 disclose a toothpaste containing urea peroxide which dissociates into urea and hydrogen peroxide in the oral cavity, in a paste carrier comprising an anionic detergent, sorbitol and glycerin humectant and a thickening agent such as gum tragacanth, sodium alginate or sodium carboxymethyl cellulose.

U.S. Pat. No. 4,405,599 discloses a toothpaste containing a combination of calcium peroxide and sodium perborate oxidizing agents, dicalcium phosphate, calcium carbonate and magnesium carbonate cleaning agents, sorbitol humectant, cornstarch, cellulose gum thickening agents, and an anionic detergent.

All of the foregoing peroxide dentifrices may be employed in the present invention.

Examples of further peroxide dentifrices which may be employed in the present invention are indicated in the following tables:

EXAMPLE A

| Ingredient | Wt. % |
| --- | --- |
| PLURONIC F127 | 20.000 |
| Glycerin | 40.000 |
| Hydrogen Peroxide (35%) | 4.285 |
| Methyl Salicylate | 0.500 |
| FD&C Blue | 0.005 |
| Phosphoric Acid (85% w/w) | 0.150 |
| Deionized water | q.s. |

EXAMPLE B

| Ingredient | Parts |
| --- | --- |
| Hydrogen peroxide (35%) | 14.30 |
| Purified water | 84.45 |
| CARBOPOL 934 | 0.50 |
| Hydroxyethyl cellulose | 0.50 |
| Triethanolamine | 0.25 |

EXAMPLE C

| Ingredient | Parts |
| --- | --- |
| Hydrogen peroxide (35%) | 11.5 |
| Distilled water | 86.6 |
| CARBOPOL 934 | 1.5 |
| Sodium lauryl sulfate, | 0.1 |
| Hydroxypropyl cellulose | 0.3 |
| Sodium hydroxide (10%) (pH 3.0–4.5) | q.s. |

EXAMPLE D

| Ingredient | Parts |
| --- | --- |
| Urea peroxide | 10.0 |
| CARBOPOL 941 | 1.5 |
| Glycerin, anhydrous | 88.5 |

EXAMPLE E

| Ingredients | Parts |
| --- | --- |
| Hydrogen Peroxide (35%) | 10.00 |
| CARBOPOL 940 | 1.50 |
| Polyethylene Glycol 400 | 30.00 |
| Glycerine 99.6% | 25.00 |
| Butylated Hydroxy Anisole | 0.50 |
| Sodium Saccharin | 0.50 |
| Mixed Flavor oils | 1.00 |
| Calcium Pyrophosphate | 29.00 |
| Sodium Lauryl Sarcosinate | 1.50 |
| Tetrasodium Pyrophosphate | 1.00 |

EXAMPLE F

| Ingredients | Parts |
| --- | --- |
| Urea peroxide (35%) | 14.3 |
| Purified water | 84.45 |
| CARBOPOL 934 | 0.5 |
| Hydroxyethyl cellulose | 0.5 |
| Triethanolamine | 0.25 |

EXAMPLE G

| Ingredients | Parts |
| --- | --- |
| Carbamide peroxide | 8.5 |
| Sodium bicarbonate | 15.0 |
| Calcium carbonate | 8.0 |
| Acidulate NaF (low pH) | 0.5 |
| Paste carrier | 68.0 |

The paste carrier of EXAMPLE G comprises a mixture of detergent, e.g. a synthetic detergent containing water, a humectant, sorbitol, and a thickening agent or binder and flavoring.

The peroxide compound dentifrices may be formulated in accordance with the procedures set forth in the following U.S. Patents: U.S. Pat. No. 5,085,853 (EXAMPLE A), U.S. Pat. No. 4,687,663 (EXAMPLES B, C and D), U.S. Pat. No. 4,895,721 (EXAMPLE E), U.S. Pat. No. 4,528,180 (EXAMPLE F) and U.S. Pat. No. 4,522,805 (EXAMPLE G), all of which are incorporated herein by reference.

In accordance with the invention, a ribbon or strip of the peroxide containing dentifrice is extruded on the bristle ends of a toothbrush along with a equal volume ribbon or strip of conventional toothpaste. Depending upon the size of the toothbrush head and whether the dentifrice and toothpaste are deployed on top of one another or end to end, from approximately 1.3 to 2.5 grams of conventional toothpaste is dispensed and from 0.7 to 1.5 grams of peroxide dentifrice is dispensed.

Typical examples of toothpaste formulations which may be employed in conjunction with a dentifrice having peroxide as its active constituent ingredient in the practice of the present invention are set forth in the following tables:

EXAMPLE 1

| Ingredient | Parts |
|---|---|
| Sorbitol and related Polyols | 62.0 |
| Hydrated Silica or Aluminum Hydroxide | 23.0 |
| Water | q.s. |
| Glycerin | 3.0 |
| SD Alcohol 38B | 2.0 |
| Sodium Lauryl Sulfate | 1.5 |
| Cellulose Gum | 1.0 |
| Sodium Monofluorophosphate | 0.7 |
| Flavor | .7 |
| Sodium Saccharin | 0.2 |
| Sodium Benzoate | 0.2 |
| Colorant | q.s. |

The abrasive constituent in such toothpaste formulation comprises Hydrated Silica or Aluminum Hydroxide.

A further example of a suitable toothpaste formulation for utilization in conjunction with the present invention is set forth in the following table:

EXAMPLE 2

| Ingredient | Parts |
|---|---|
| Water | q.s. |
| Hydrated Silica or Aluminum Hydroxide | 40.0 |
| Glycerin | 25.0 |
| Sorbitol | 15.0 |
| Tetrasodium Pyrophosphate | 5.0 |
| Sodium Lauryl Sulfate | 1.5 |
| Cellulose Gum | 1.2 |
| PEG-12 | 1.0 |
| PVM/MA Copolymer | 1.0 |
| Sodium Fluoride | 0.2 |
| Sodium Saccharin | 0.2 |
| Sodium Hydroxide | 0.1 |
| Flavor | 0.7 |
| Colorant | q.s. |

As with Example 1, the abrasive constituent in the above toothpaste formulation is Hydrated Silica or Aluminum Hydroxide. The Hydrated Silica or Aluminum Hydroxide contained therein is in a higher concentration than in Example 1. The toothpaste formulation of Example 2 utilizes a higher percentage of abrasive material, Hydrated Silica for the purpose of providing a tartar control or anti-tartar abrasive formulation. Additional constituents of such formulation which may provide anti-tartar characteristics include Tetrasodium Pyrophosphate and PVM/MA Copolymer.

A further suitable toothpaste formulation is set forth in the following table:

EXAMPLE 3

| Ingredient | Parts |
|---|---|
| Sorbitol | 33.0 |
| Hydrated Silica or Aluminum Hydroxide | 24.0 |
| Water | q.s. |
| Glycerin | 10.0 |
| Tetrasodium Phosphate | 5.0 |
| Sodium Lauryl Sulfate | 1.5 |
| Cellulose Gum | 1.3 |
| Flavor | 0.7 |
| PEG-12 | 0.5 |
| Sodium Fluoride | 0.25 |
| Sodium Saccharin | 0.2 |
| Colorant | q.s. |

An additional suitable toothpaste formulation is set forth in the following table:

EXAMPLE 4

| Ingredient | Parts |
|---|---|
| Sorbitol | 40.0 |
| Calcium Carbonate | 30.0 |
| Water | q.s. |
| Hydrated Silica | 10.0 |
| Sodium Lauryl Sulfate | 1.5 |
| Cellulose Gum | 1.3 |
| Sodium Monofluorophosphate | 0.7 |
| Flavor | .7 |
| Calcium Carrageenan | 0.5 |
| PEG-8 | 0.5 |
| Titanium Dioxide | 0.2 |
| Sodium Saccharin | 0.2 |
| Sodium Benzoate | 0.2 |
| Colorant | q.s. |

It should be noted that the abrasive constituent in Example 4 comprises 30% Calcium Carbonate.

A further toothpaste formulation suitable for employment in conjunction with the present invention is set forth in the following table:

EXAMPLE 5

| Ingredient | Parts |
|---|---|
| Sorbitol | 30.0 |
| Water | q.s. |
| Hydrated Silica or Aluminum Hydroxide | 25.0 |
| Trisodium Phosphate | 5.0 |
| Sodium Lauryl Sulfate | 1.5 |
| Carbomer 956 | 1.0 |
| Xanthan Gum | 0.7 |
| Flavor | 0.7 |
| Sodium Fluoride (.15% fluoride by volume) | 0.2 |
| Sodium Phosphate | 0.2 |
| Sodium Saccharin | 0.2 |
| Titanium Dioxide | 0.2 |
| Colorant | q.s. |

A further toothpaste formulation suitable for employment in the present invention is set forth in the following table:

EXAMPLE 6

| Ingredient | Parts |
|---|---|
| Dicalcium Phosphate Dihydrate | 45.0 |

-continued

| Ingredient | Parts |
| --- | --- |
| Water | q.s. |
| Glycerin | 35.0 |
| Sodium Lauryl Sulfate | 1.5 |
| Cellulose Gum | 1.2 |
| Sodium Monofluorophosphate | 0.7 |
| Flavor | 0.75 |
| Sodium Benzoate | 0.2 |
| Tetrasodium Pyrophosphate | 0.2 |
| Sodium Saccharin | 0.2 |

An additional toothpaste formulation is set forth in the following table:

EXAMPLE 7

| Ingredient | Parts |
| --- | --- |
| Calcium Carbonate | 45.7 |
| Starch | 7.0 |
| Glycerol | 28.2 |
| Water | 14.4 |
| Sodium Benzoate | 2.2 |
| Flavoring | 1.3 |
| Sodium Lauryl Sulfate | 1.2 |

It should be appreciated that the system of the present invention functions with any extrudable dentifrice formulation having a peroxide compound constituent. Included among such dentifrices are those containing a hydrogen peroxide constituent such as the dentifrices disclosed in U.S. Pat. No. 5,084,268, incorporated herein by reference; U.S. Pat. No. 4,980,152; U.S. Pat. No. 4,839,156 and Examples A, B, C, and E. Also included are dentifrices containing urea peroxide, such as Examples D and F, dentifrices containing carbamide peroxide, such as Example G and dentifrices containing calcium peroxide, such as those disclosed in U.S. Pat. No. 4,405,599 and U.S. Pat. No. 4,980,154, both of which are incorporated herein by reference. Numerous additional peroxide compound dentifrice formulations are commercially available.

Pursuant to the invention, equal volumes of peroxide containing dentifrice and conventional toothpaste are extruded onto the ends of bristles of a toothbrush and the toothbrush is inserted into the oral cavity with the user brushing teeth interdental spaces and gingival tissue in a normal fashion with conventional brush strokes. It has been found that the constituents of conventional toothpaste present an environment which accelerates the breakdown of the peroxide compound constituent and the generation of active oxygen within the oral cavity. At least one factor involved in the mechanism involving the accelerated breakdown of the peroxide constituent of the dentifrice is the fact that conventional toothpastes include pH elevating constituents and at elevated pH levels, hydrogen peroxide decomposes more readily.

It is believed that a major factor in the accelerated breakdown of the hydrogen peroxide constituent is the abrasive constituent of the conventional toothpaste. In many instances, the abrasive constituent of a conventional toothpaste comprises Hydrated Silica (Example 1, Example 2, Example 3 and Example 5). In other instances, the abrasive constituent comprises Calcium Carbonate (Example 4 and Example 7). While in other toothpaste formulations, the abrasive constituent comprises Dicalcium Phosphate Dihydrate (Example 6). These abrasive compounds comprise metal salts which reduce the peroxide to initiate the release of oxygen. Further conventional toothpaste constituents which are believed to accelerate the decomposition of Hydrogen Peroxide include Sodium Fluoride, Sodium Monofluorophospate, Tetrasodium Pyrophosphate, Tetrasodium Phosphate, Titanium Dioxide, Cellulose Gum, Sodium Hydroxide, Trisodium Phosphate and Sodium Phosphate.

It has also been observed that brushing with a mixture of both conventional toothpaste and a dentifrice having a Hydrogen Peroxide constituent results in enhancement of the flavoring of the conventional toothpaste. While the exact mechanism of such enhancement is unknown, it is believed that the generation of free oxygen within the oral cavity includes, among its beneficial effects, the enhancement of taste sensitivity.

An additional beneficial result of practicing the method of the present invention results in reduced dentin abrasion levels. A laboratory study has been conducted to determine the relative abrasiveness of a mixture containing equal portions of STAY-WHITE dentifrice and a toothpaste sold under the trademark COLGATE® Tartar Control. The test comprised brushing dentin specimens for 1,500 strokes using a slurry consisting of 25 gm Colgate Tartar Control in 40 ml water, a further slurry consisting of a mixture of 12.5 gm STAY-WHITE® peroxide dentifrice and 12.5 gm Colgate Tartar Control in 40 ml water and a reference slurry consisting of 10 gm ADA reference abrasive in 50 ml of 0.5% CMC glycerin solution.

The ADA reference abrasive was assigned a value of 100 and its ratio to the test material was calculated.

The results of such test are reported in the table below:

| Specimen | Dentin Abrasion Level Colgate Tartar Control | Dentin Abrasion Level Stay-White + Colgate Tartar Control |
| --- | --- | --- |
| 1 | 92.27 | 73.51 |
| 2 | 94.04 | 68.86 |
| 3 | 124.70 | 78.98 |
| 4 | 90.97 | 71.66 |
| 5 | 106.84 | 55.06 |
| 6 | 122.53 | 66.56 |
| 7 | 105.66 | 53.88 |
| 8 | 95.57 | 68.20 |

From the results of such test it was concluded that when mixed in equal proportions, the combination of STAY-WHITE and Colgate Tartar Control toothpaste was significantly less abrasive to human dentin than utilizing Colgate Tartar Control toothpaste alone.

Thus, it will be seen that there is provided an oral hygiene system which achieves the various aspects, features and considerations of the present invention and which is well suited to meet the conditions of practical usage.

Since various possible embodiments might be made of the invention described herein without departing from the spirit of same, and various changes might be made in the exemplary embodiments set forth, it should be understood that all matters herein described are to be interpreted as illustrative, rather than in a limiting sense.

Having thus described the invention, there is claimed as new and desired to be secured by Letters Patent:

1. A method of cleansing tooth surfaces while reducing dentin abrasion which occurs during tooth brushing with a conventional abrasive-containing toothpaste, which comprises the steps of:

(a) providing a sufficient amount of a conventional toothpaste and containing from 20% to 50% by weight of an abrasive agent selected from the group consisting of hydrated silica, aluminum hydroxide, calcium carbonate, and dicalcium phosphate dihydrate;

(b) providing a sufficient amount of non-abrasive, homogeneously dispersed dentifrice comprising from 0.2% to 15% by weight of a peroxide compound, based upon the weight of total dentifrices;

(c) providing a toothbrush having bristles, the bristles having ends;

(d) placing the amount of conventional toothpaste from step (a) and the amount of dentrifice from step (b) in strips on the bristle ends, the strip being in other than side by side relationship;

(e) admixing the conventional toothpaste from step (a) with the dentifrice from step (b) to accelerate the release of oxygen from the dentifrice; and (f) brushing tooth surfaces with the admixture from step (e).

2. The method of claim 1 wherein the volume amount of conventional toothpaste in step (a) is substantially equal to the volume amount of dentifrice in step (b).

3. The method of claim 1 wherein the mixture in step (c) comprises from 1.3 to 2.5 grams of conventional toothpaste and from 0.7 to 1.5 grams of dentifrice.

4. The method of claim i wherein the conventional toothpaste also contains one or more compounds selected from the group consisting of sodium fluoride, sodium monofluorophosphate, tetrasodium pyrophosphate, tetrasodium phosphate, titanium dioxide, cellulose gum, sodium hydroxide, trisodiumphosphate, and sodium phosphate, in an amount sufficient to accelerate decomposition of the peroxide compound.

5. The method of claim 1 wherein step (f) includes the step of placing the bristles of the toothbrush in the oral cavity and brushing tooth and gum surfaces.

6. The method of claim 1 wherein the peroxide compound is selected from the group consisting of hydrogen peroxide, urea peroxide, carbamide peroxide, and calcium peroxide.

7. A method of oral hygiene which reduces dentin abrasion normally occurring during tooth brushing with a conventional abrasive-containing toothpaste, the method comprising the steps of:

placing a strip of conventional abrasive-containing toothpaste containing from 20% to 50% by weight of an abrasive agent selected from the group consisting of hydrated silica, aluminum hydroxide, calcium carbonate, and dicalcium phosphate dihydrate and a strip of a non-abrasive, aqueous, homogeneously dispersed dentifrice comprising from 0.2% to 15% by weight of peroxide compound based upon the weight of the total dentifrice on the bristle ends of a toothbrush with the strips placed in other than side by side relationship, (b) admixing the toothpaste and dentrifice; and (c) brushing tooth surfaces with the admixture from step (b).

8. The method of claim 7 wherein in step (a) the volume amount of conventional toothpaste is substantially equal to the volume amount of dentifrice.

9. The method of claim 7 wherein the mixture in step (b) comprises from 1.3 to 2.5 grams of conventional toothpaste and from 0.7 to 1.5 grams of dentifrice.

10. The method of claim 7 wherein the conventional toothpaste also contains one or more compounds selected from the group consisting of sodium fluoride, sodium monofluorophosphate, tetrasodium pyrophosphate, tetrasodium phosphate, titanium dioxide, cellulose gum, sodium hydroxide, trisodium phosphate, and sodium phosphate, in an amount sufficient to accelerate decomposition of the peroxide compound.

11. The method of claim 7 wherein step (a) includes the step of providing a toothbrush and dispensing substantially equal volumes of dentifrice and toothpaste on the bristles of the toothbrush, and step (b) includes the step of placing the bristles of the toothbrush in the oral cavity and brushing tooth and gum surfaces.

12. The method of claim 7 wherein the peroxide compound is selected from the group consisting of hydrogen peroxide, urea peroxide, carbamide peroxide, and calcium peroxide.

13. The method of claim 1 wherein step (d) includes placing the strips in end-to-end relationship.

14. The method of claim 1 wherein step (d) included placing one of the strips on top of the other strip.

15. The method of oral hygiene which reduces dentin abrasion normally occurring during tooth brushing with a conventional abrasive-containing toothpaste in accordance with claim 7 wherein one of the strips is placed on top of the other strip.

16. The method of oral hygiene which reduces abrasion normal occurring during tooth brushing with a conventional abrasive containing toothpaste in accordance with claim 7 wherein the strips are placed in end-to-end relationship.

* * * * *